(12) United States Patent
Brink

(10) Patent No.: US 7,865,238 B2
(45) Date of Patent: *Jan. 4, 2011

(54) HIGH-VOLTAGE MODULE FOR AN EXTERNAL DEFIBRILLATOR

(75) Inventor: Gregory D. Brink, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 655 days.

This patent is subject to a terminal disclaimer.

(21) Appl. No.: 11/575,764

(22) PCT Filed: Sep. 12, 2005

(86) PCT No.: PCT/IB2005/052981

§ 371 (c)(1), (2), (4) Date: Mar. 22, 2007

(87) PCT Pub. No.: WO2006/035333

PCT Pub. Date: Apr. 6, 2006

(65) Prior Publication Data

US 2007/0299474 A1 Dec. 27, 2007

Related U.S. Application Data

(60) Provisional application No. 60/614,452, filed on Sep. 29, 2004, provisional application No. 60/651,432, filed on Feb. 8, 2005.

(51) Int. Cl.
*A61N 1/00* (2006.01)
(52) U.S. Cl. ........................................................ 607/7
(58) Field of Classification Search .................... 600/5, 600/7
See application file for complete search history.

(56) References Cited

U.S. PATENT DOCUMENTS

| 3,867,950 | A | * | 2/1975 | Fischell ........................ 607/33 |
| 5,741,313 | A | | 4/1998 | Davis et al. |
| 5,824,017 | A | | 10/1998 | Sullivan et al. |
| 6,057,175 | A | | 5/2000 | Milla et al. |
| 6,181,004 | B1 | | 1/2001 | Koontz et al. |
| 6,441,513 | B1 | * | 8/2002 | Mulhauser ................... 307/130 |
| 6,960,945 | B1 | * | 11/2005 | Bonin ........................ 327/111 |
| 2003/0011967 | A1 | * | 1/2003 | Nielsen et al. .............. 361/517 |
| 2003/0204216 | A1 | | 10/2003 | Ries et al. |
| 2004/0068301 | A1 | | 4/2004 | Waltman et al. |

* cited by examiner

*Primary Examiner*—George Manuel
*Assistant Examiner*—Shubatra Narayanaswamy
(74) *Attorney, Agent, or Firm*—W. Brinton Yorks, Jr.

(57) ABSTRACT

A defibrillator includes a module having a portion of the high-voltage components of the defibrillator attached to a substrate and encased in a dielectric material. In one embodiment the defibrillating shock is delivered by a high voltage H-bridge circuit which utilizes four controllably switched semiconductor devices such as IGBTs.

19 Claims, 14 Drawing Sheets

HIGH-VOLTAGE MODULE FOR AN EXTERNAL DEFIBRILLATOR

This application claims the benefit of U.S. provisional application Ser. Nos. 60/614,452 and 60/651,432 filed Sep. 29, 2004, and Feb. 8, 2005, respectively, which are incorporated herein.

The present invention relates generally to external defibrillators, and more particularly, relates to defibrillators having compact and modular designs for high-voltage components of the defibrillator.

Sudden cardiac arrest (SCA) most often occurs without warning, striking people with no history of heart problems. It is estimated that more than 1000 people per day are victims of sudden cardiac arrest in the United States alone. SCA results when the electrical component of the heart no longer functions properly causing an arrhythmia. One such arrhythmia, ventricular fibrillation (VF), is caused by abnormal and very fast electrical activity in the heart. As a result, the heart fails to adequately pump blood through the body. VF may be treated by applying an electric shock to a patient's heart through the use of a defibrillator.

Defibrillators include manual defibrillators, automatic or semi-automatic external defibrillators (AEDs), defibrillator/monitor combinations and advisory defibrillators. The shock delivered by a defibrillator clears the heart of abnormal electrical activity (in a process called "defibrillation") by producing a momentary asystole and providing an opportunity for the heart's natural pacemaker areas to restore a normal cardiac rhythm. Currently available external defibrillators provide either a monophasic or biphasic electrical pulse to a patient through electrodes applied to the chest. Monophasic defibrillators deliver an electrical pulse of current in one direction, whereas biphasic defibrillators deliver an electrical pulse of current first in one direction and then in the opposite direction. When delivered external to the patient, these electrical pulses are high energy pulses, typically in the range of 50 Joules for pediatric patients to 200 Joules for adults.

External defibrillators are typically located and used in hospital emergency rooms, public facilities, and emergency medical vehicles. Of the wide variety of external defibrillators currently available, automatic and semi-automatic external defibrillators (AEDs) are becoming increasingly popular because they can be used by relatively inexperienced personnel. Such defibrillators can also be especially lightweight, compact, and portable, enabling their immediate use even when experienced medical personnel have not arrived to attend to a patient. In order to do this, the medical expertise of the medical professional must be replaced with precise information processors which can be programmed to analyze an ECG waveform and reliably determine if and when a defibrillating shock is to be applied to the patient. Additionally it is desirable that AEDs be as lightweight and compact as possible for easy portability.

These demands mean that low voltage processors and integrated circuitry must share an AED package with the high voltage components of the shock delivery circuitry. To prevent interference or damage to the low voltage circuitry care must be taken in locating components in the package so that the low voltage components are sufficiently isolated and separated from the high voltage components. Generally this has been accomplished by locating the high voltage components on their own area of the unit's printed circuit board and by following component layout and design rules which adequately separate the high voltage components from the low voltage components and conductors. Unfortunately abiding by these design rules tends to make an AED bulkier than is otherwise desirable. Accordingly it is desirable to be able to package the components of an AED as compactly as possible and, if possible, even more compactly than the design rules would dictate, but without exposing the low voltage components and conductors to the hazards of arcing or discharge from high voltage conductors and components of the unit.

Conventional design rules for high-energy and high-voltage systems such as an external defibrillator place constraints on the layout of high-voltage components of the defibrillator. The constraints on component spacing will limit how compact a defibrillator can be. For example, using conventional design rules, high-voltage components of the defibrillator have a minimum distance requirement in their placement relative to one another. Additionally, conventional designs for defibrillators utilize high-voltage components that are packaged in device packages rated for high-voltage, high-energy environments. These device packages typically have relatively larger and bulkier package profiles than lower rated device packages. The spacing requirements and device package design for conventionally designed defibrillators result in an inefficient layout of the high-voltage components of the defibrillator, which consequently makes designing more compact defibrillators difficult. Therefore, there is a need for a compact design for high-voltage components of a defibrillator.

In accordance with the principles of the present invention high voltage components of an AED unit are packaged together and separated from other components by a non-air dielectric which insulates the high voltage components and prevents damage to nearby low voltage components and conductors. The non-air dielectric enables the high voltage components to be packaged more densely than the separation design rules would otherwise allow, aided by the low duty cycle of their use which limits the need for heat dissipation.

In one aspect of the present invention, a defibrillator includes a module having high-voltage components, such as a steering circuit, attached to a substrate and encased in a dielectric material. The steering circuit is coupled to a storage capacitor electrically charged by a charging circuit and directs the stored electric energy through a pair of electrodes to deliver defibrillating energy to a patient. In another aspect of the present invention, a transformer of the charging circuit is also attached to the substrate and encased in the dielectric material. The high-voltage components attached to the substrate can be packaged in device packages rated below the voltage and energy operating conditions to which the defibrillator is subject during delivery of defibrillating energy to a patient.

In accordance with a further aspect of the present invention the high voltage bridge circuit used to deliver pulses to the patient of a desired period and polarity is formed primarily or entirely of IGBT devices. The IGBT devices enable the switching elements of the bridge circuit to be controllably turned off, enabling the circuit to be used for related lower voltage applications such as pacing.

IN THE DRAWINGS

Embodiments of the present invention are directed to a defibrillator that includes a compact high-voltage module having high-voltage electronics of the defibrillator placed in proximity to one another and encased in a dielectric material. In the following description well-known circuits have not been shown in detail in order to avoid unnecessarily obscuring the description of the various embodiments of the invention. Also not presented in any great detail are those well-known control signals and signal timing protocols associated with the internal operation of defibrillators.

Figure 1:
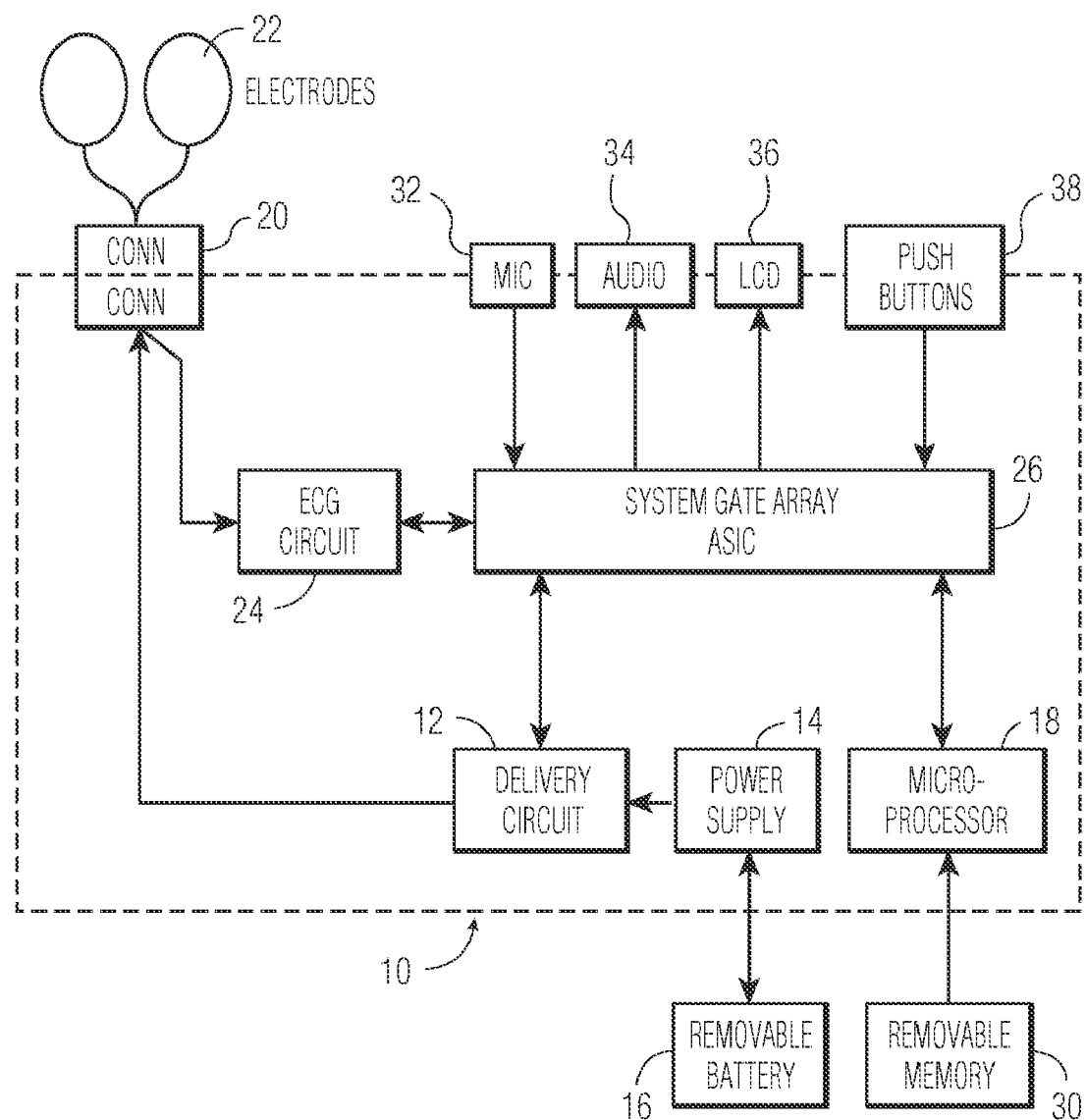
FIG. 1 is a functional block diagram of an external defibrillator according to an embodiment of the present invention.

FIG. 1 is a functional block diagram of a defibrillator or AED 10 according to an embodiment of the present invention. The AED 10 includes a delivery circuit 12 that is capable of delivering high or low voltage depending upon the application. The AED 10 further includes a power supply 14 which is powered by an energy source such as a removable battery 16 which provides power to components of the AED 10, including the high-voltage delivery circuit 12. A microcontroller or processor 18 controls the operation of the various components of the AED 10. The high-voltage delivery circuit 12 delivers a pulse of electrical energy to a patient via an electrode connector or interface 20 and electrodes 22.

An electrocardiogram (ECG) circuit 24 acquires and processes the patient's ECG signals acquired through the electrodes 22 and sends the signals to the processor 18 via a system gate array 26. The system gate array 26 is a custom application-specific integrated circuit (ASIC) integrating many of the defibrillator functions (including user interface control and many of the internal functions) and interfacing the processor 18 with other components of the AED 10. Providing the separate system gate array or ASIC 26 allows the processor 18 to focus on other tasks. The functionality of the ASIC 26 can be included within the operations performed by the processor 18 as well, or can be replaced by discrete logic circuit components or a separately dedicated processor.

The AED 10 also includes a memory device 30 (such as a removable Personal Computer Memory Card International Association (PCMCIA) card, flash memory or magnetic tape), and user interface components such as a microphone 32, an audio speaker 34, an LCD display panel 36, and a set of push-button controls 38. Those skilled in the art will understand that a number of other components may be included within the AED 10 (e.g., a system monitor and associated status indicators), but are not shown in order to avoid unnecessarily obscuring the description of embodiments of the present invention.

Figure 2:
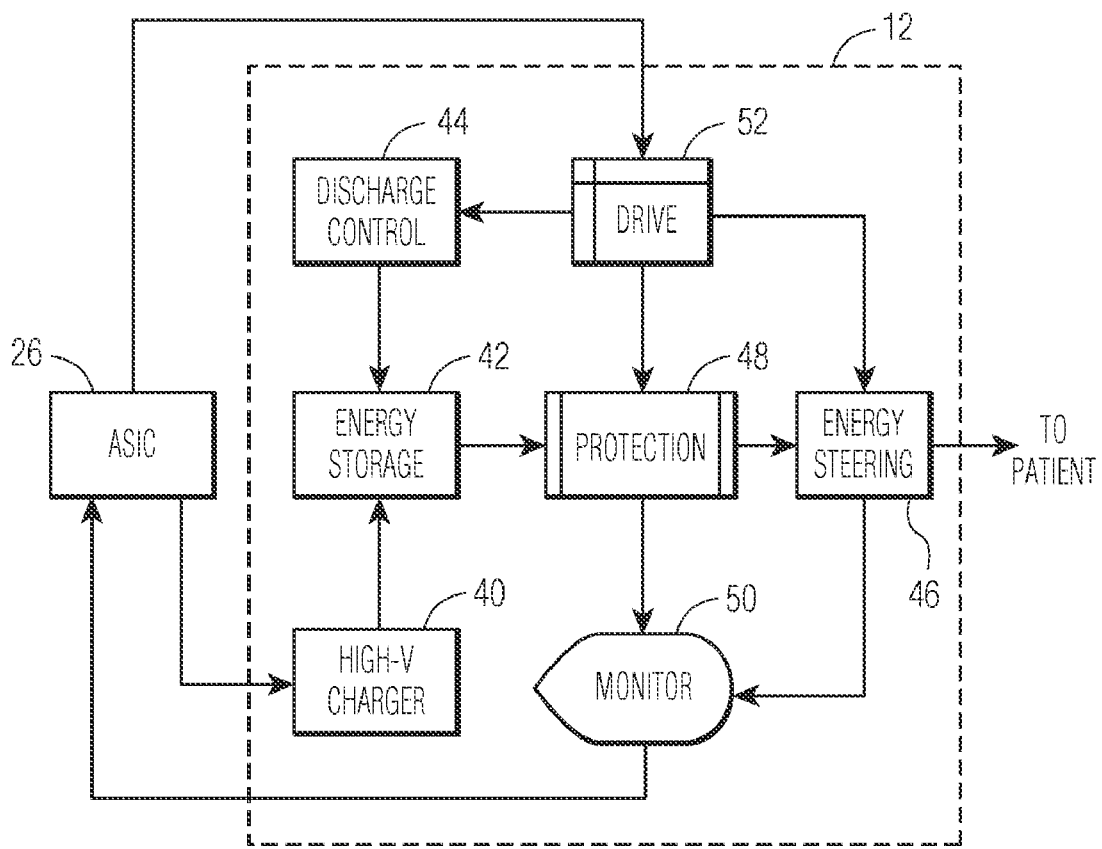
FIG. 2 is a functional block diagram of a high-voltage delivery circuit included in the defibrillator of FIG. 1.

As shown in FIG. 2, the high-voltage delivery circuit 12 includes a number of functional circuit blocks which are both monitored and controlled by the ASIC 26. A high-voltage charging circuit 40, such as a flyback power supply, responds to one or more control signals issued by the ASIC 26 and generates electrical energy for provision to an energy storage circuit 42. The storage circuit 42 stores the electrical energy for subsequent delivery to the patient. The storage circuit 42 is typically a storage capacitor. A discharge control circuit 44 controls discharge of the energy stored in the storage circuit 42 to an energy transfer or steering circuit 46 through a protection circuit 48. The steering circuit 46 in turn delivers the electrical energy to the patient via the connector 20 and electrodes 22 (FIG. 1). The steering circuit 46 may deliver the electrical energy to the patient with a single polarity (e.g., a monophasic pulse) or with an alternating polarity (e.g., a biphasic or multiphasic pulse), as required by the desired implementation.

The protection circuit 48 functions to limit energy delivery from the storage circuit 42 to the steering circuit 46 (and hence to the patient) and to discharge or otherwise disarm the storage circuit 42 in the event of a fault condition. The protection circuit 48 operates to limit the time-rate-of-change of the current flowing through the steering circuit. A monitor circuit 50 senses operations of both the protection circuit 48 and the steering circuit 46 and reports the results of such monitoring to the ASIC 26. The above-described operations of the discharge control circuit 44, the steering circuit 46, and the protection circuit 48 are controlled by a drive circuit 52 issuing a plurality of drive signals. Operation of the drive circuit 52 is, in turn, controlled by one or more control signals provided by the ASIC 26.

Figure 3:
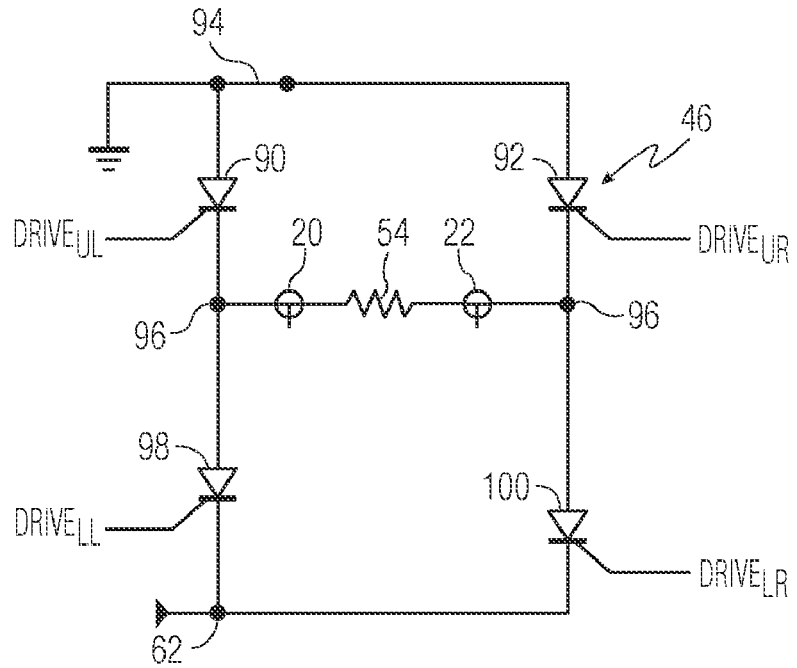
FIG. 3 is a schematic diagram of an energy steering circuit of the high-voltage delivery circuit shown in FIG. 2.

FIG. 3 illustrates the energy steering circuit 46 according to an embodiment of the present invention. The energy steering circuit 46 is of an "H-bridge" configuration, with four switching elements. The switching elements are preferably silicon controlled rectifiers (SCRs), but other switching elements can also be used in alternative embodiments. The steering circuit 46 includes an upper-left (UL) switching element, such as SCR 90, and an upper-right (UR) switching element, such as SCR 92. The anode of each of SCR 90 and SCR 92 is connected to a reference voltage source 94, such as ground potential. The cathode of each of SCR 90 and SCR 92 is connected to a respective one of two patient terminals 96 (which, in turn, are coupled with the connector 20 and a respective electrode 22 of FIG. 1). The control terminal or gate of each of SCR 90 and SCR 92 receives an UL or UR drive signal produced by the drive circuit 52 (FIG. 2) to selectively switch the SCRs on. A patient is represented by a resistor 54, shown in the electrical location of the patient during circuit operation.

The steering circuit 46 also includes a lower-left (LL) switching element, such as SCR 98, and a lower-right (LR) switching element, such as SCR 100. The anode of each of SCR 98 and SCR 100 is connected to one of the patient terminals 96. The cathode of each of SCR 98 and SCR 100 is connected to a lower terminal or node 62. As previously discussed with reference to FIG. 2, the energy stored in the storage circuit 42 is provided to the node 62 through the protection circuit 48. The control terminal or gate of each of SCR 98 and SCR 100 receives a LL or LR drive signal from the drive circuit 52 (FIG. 2) to selectively switch the SCRs on. As desired, the monitor circuitry 50 of FIG. 2 can advantageously sense the voltage of the node 62 and provide such information to the ASIC 26. Alternatively, time integration of monitored current flow can provide information corresponding to voltages during patient defibrillation.

Figure 4:
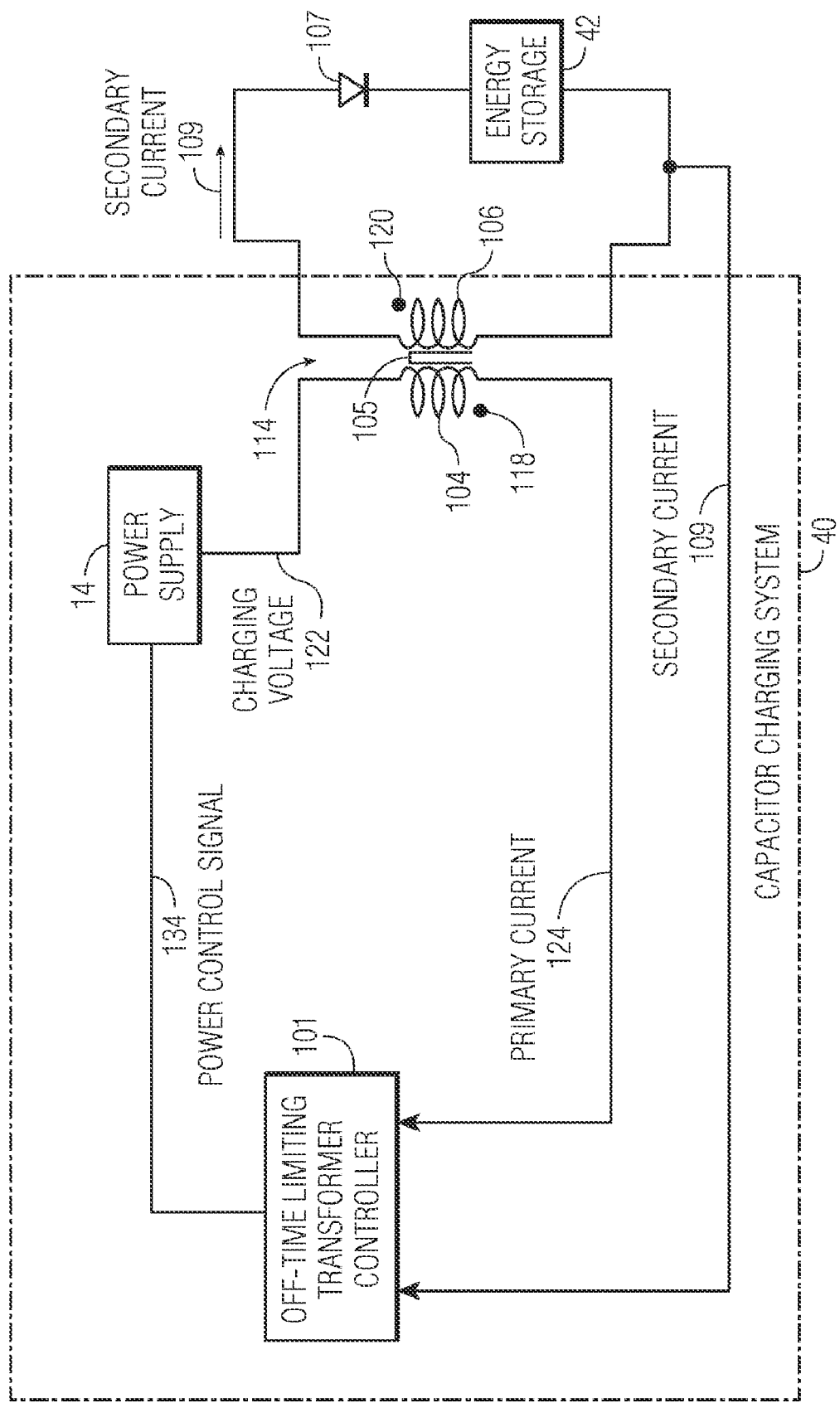
FIG. 4 is a schematic diagram of a high-voltage charging circuit of the high-voltage delivery circuit shown in FIG. 2.

FIG. 4 illustrates the high-voltage charging circuit 40 according to an embodiment of the present invention. The high-voltage charging circuit 40 includes a transformer 114. The transformer 114 includes a core 105, primary winding 104 and secondary winding 106. In the particular embodiment illustrated in FIG. 4, the primary winding 104 and the secondary winding 106 form a fly-back transformer and, therefore, are out of phase with each other. This is shown by the polarity indicating indicia 118 and 120. As such, the following description sets forth various embodiments and components of the high-voltage charging circuit 40 for driving a fly-back transformer to generate current waveform 109. The current 109 flows through the secondary winding 106 in the direction shown to transfer energy to the storage circuit 42 which is connected across the secondary winding 106 through a high voltage rectifier diode, referred to herein as fly-back diode 107. A transformer controller 101 coupled to the primary winding 104 and the power supply 14 via power control signal 134 directly controls the duty cycle and frequency of a primary current 124.

In operation, the primary winding 104 transfers energy from a power source to the transformer core 105 when current flows through the primary winding 104. Similarly, the secondary winding 106 transfers energy from the transformer core 105 to the storage circuit 42 when the secondary current 109 is flowing through the secondary winding 106. As the primary current 124 flows through the primary winding 104, the secondary current 109 does not flow through the secondary winding 106 due to the opposing polarity of the windings. Energy that is transferred from the power supply 14 to the transformer core 105, then, is not transferred immediately to the storage circuit 42, but is instead stored within the transformer core 105. As a result, the energy stored in the transformer core 105 accumulates as the primary current 124 flows through the primary winding 104. Conversely, when the primary current 124 does not flow through the primary winding 104, the secondary current 109 flows through the secondary winding 106. When this occurs, energy previously stored in the transformer core 105 is transferred to the storage circuit 42.

Figure 5:
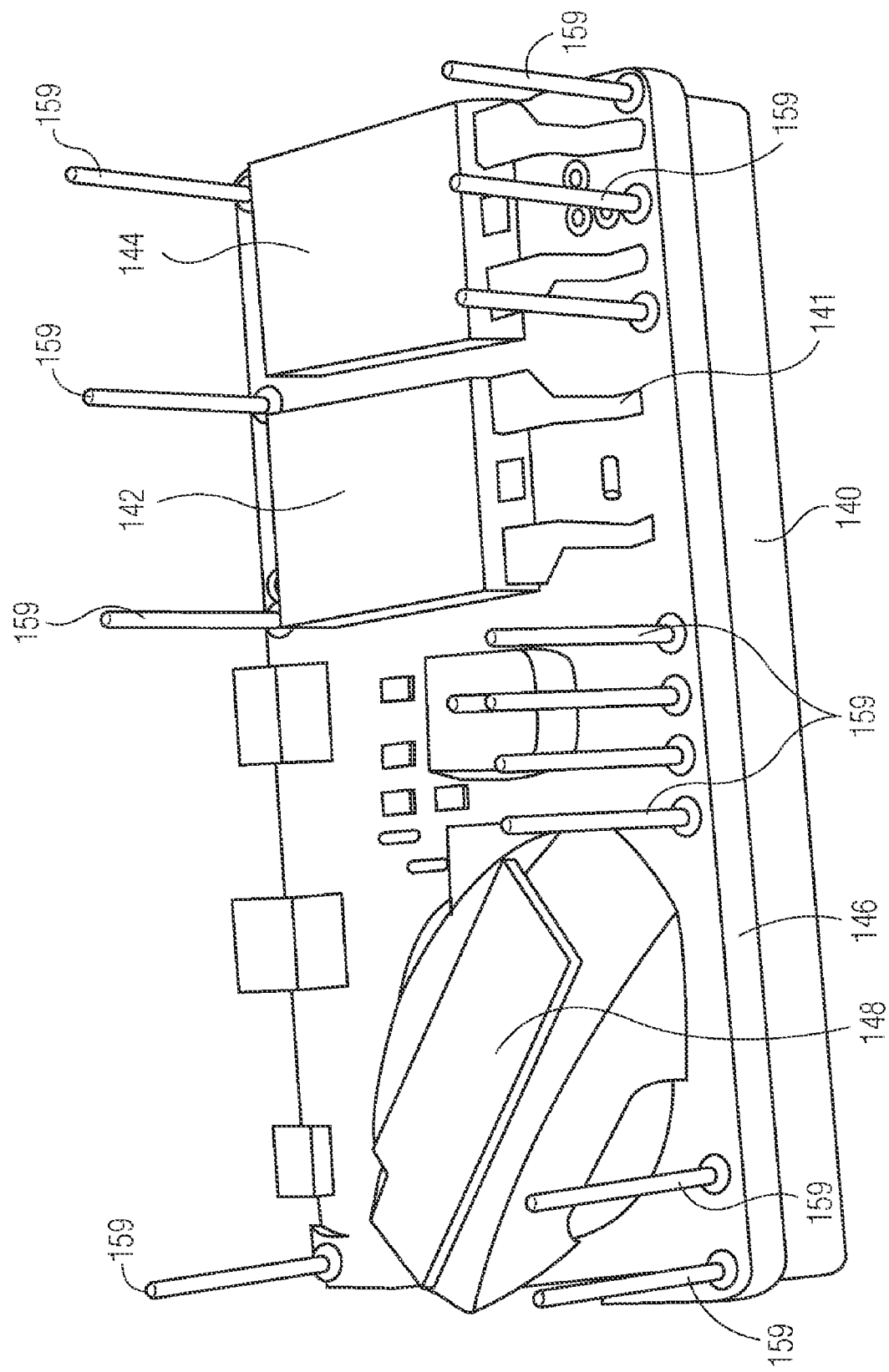
FIG. 5 is a perspective drawing of a first side of high-voltage electronics attached to a substrate for the high-voltage module according to an embodiment of the present invention.

FIG. 5 illustrates various high-voltage components of the high-voltage delivery circuit 12 (FIG. 2) attached to a first side 141 of a substrate 140 according to an embodiment of the present invention. The substrate 140 is typically a printed circuit board (PCB). Various materials known in the art, or that will be later developed, can be employed without departing from the scope of the present invention. For example, materials such as FR4, Teflon, polyimide, ceramic, and the like can be used. Additionally, the high-voltage components of the high-voltage delivery circuit 12 that are attached to the substrate 140 can vary without departing from the scope of the present invention. That is, in some embodiments, all of the high-voltage components are attached to a substrate, whereas, in alternative embodiments, only some of the high-voltage components are arranged on a substrate.

A first switching element 142 and a second switching element 144 of the energy steering circuit 46 (FIG. 2) are attached proximate to one another. A first winding 146 of a planar transformer 148 is also attached to the substrate 140, which corresponds to the transformer 114 (FIG. 4) of the high-voltage charger 40. Signal pins 159 extend from the surface of the first side 141 of the substrate 140. The dimensions of the substrate to which the first and second switching elements 142, 144 and the planar transformer 148 are attached are approximately 1.25 inches by 2.25 inches. In alternative embodiments, the substrate to which the high-voltage components are attached can have different dimensions than the substrate 140 shown in FIG. 5. In one embodiment of the present invention, the substrate has dimensions such that one side of the substrate has a surface area of less than five square inches.

In contrast to high-voltage components for conventional defibrillators, the high-voltage components for the embodiment of the present invention shown in FIG. 5 can be packaged in standard device packages that are not rated for the electrical energy and other operating conditions to which the high-voltage components are subjected during operation. For example, as previously mentioned, a defibrillating pulse delivered by the defibrillator can be as high as 2,000 volts and between 30-360 Joules of defibrillating energy. Contrary to conventional designs, the high-voltage components, such as the first and second switching elements 142, 144 of the energy steering circuit 46, are packaged in device packages that are not rated for these operating conditions. However, the device package for the switching elements 142, 144 do have package profiles that are smaller than the high-voltage packages which are characteristic of the switching elements of conventional defibrillators. As a result, the smaller device package profiles allow for the proximate placement of the switching elements 142, 144, as well as other high-voltage components, on the substrate 140.

Additionally, contrary to conventional defibrillator designs, constraints on the placement of high-voltage components relative to one another are relaxed in embodiments of the present invention. As previously discussed, high-voltage components are spaced apart by at least a minimum distance based on the magnitude of electrical energy handled by the components in conventional defibrillator designs. However, as will be explained in more detail below, in embodiments of the present invention the high-voltage components are encased in a dielectric material to allow the high-voltage components to be spaced apart by less distance than the distances of conventional designs.

Figure 6:
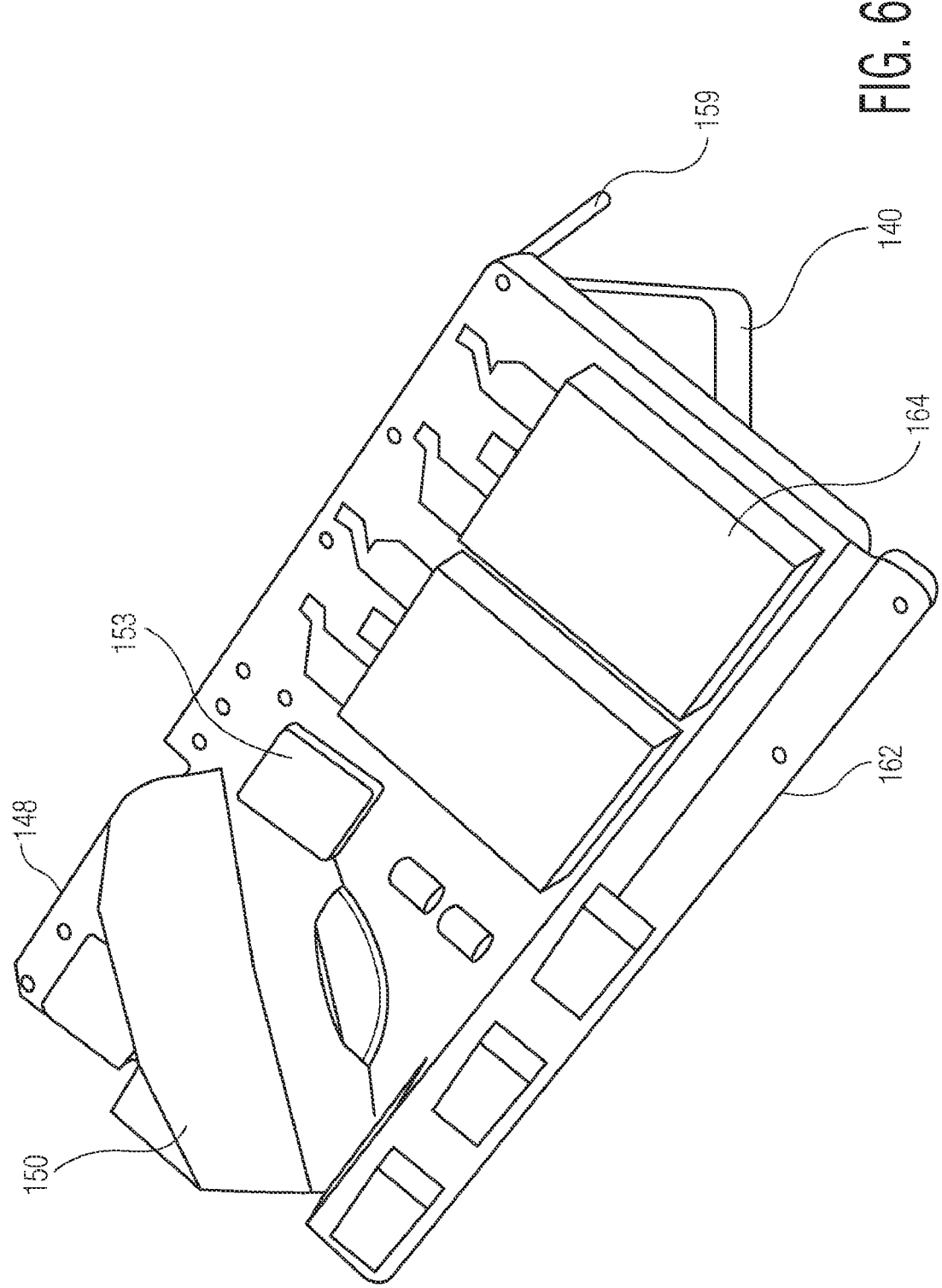
FIG. 6 is a perspective drawing of a second side of the high-voltage electronics attached to the substrate for the high-voltage module of FIG. 5.

FIG. 6 illustrates a second side 153 of the substrate 140 having additional high-voltage components attached to the surface in accordance with an embodiment of the present invention. Attaching high-voltage components of the high-voltage delivery circuit 12 (FIG. 2) to the second side 153 of the substrate 140 can be used to further reduce the size of the resulting high-voltage module. A second winding 150 of the planar transformer 148 is positioned at a first end of the substrate 140, and third and fourth switching elements 162 and 164 of the energy steering circuit 46 (FIG. 2) are positioned in proximity to one another and to a second end of the substrate 140. The second winding 150 of the planar transformer 148 is similarly positioned on the second side 153 of the substrate 140 as was the first winding 146 on the first side 141. Additionally, the third and fourth switching elements 162, 164 are also similarly positioned on the second side 153 as were the first and second switching elements 142, 144 on the first side 141. As a result, the first and second windings 146, 150 of the transformer 148 and the first and second switching elements 142, 144 and the third and fourth switching elements 162, 164 are symmetrically positioned relative to one another and to the plane of the substrate 140. Although the high-voltage components on the first and second sides 141, 153 of the substrate 140 are shown in FIGS. 5 and 6 as having a symmetrical layout, alternative embodiments of the present invention may have alternative, asymmetrical layouts for the high-voltage components.

Figure 7:
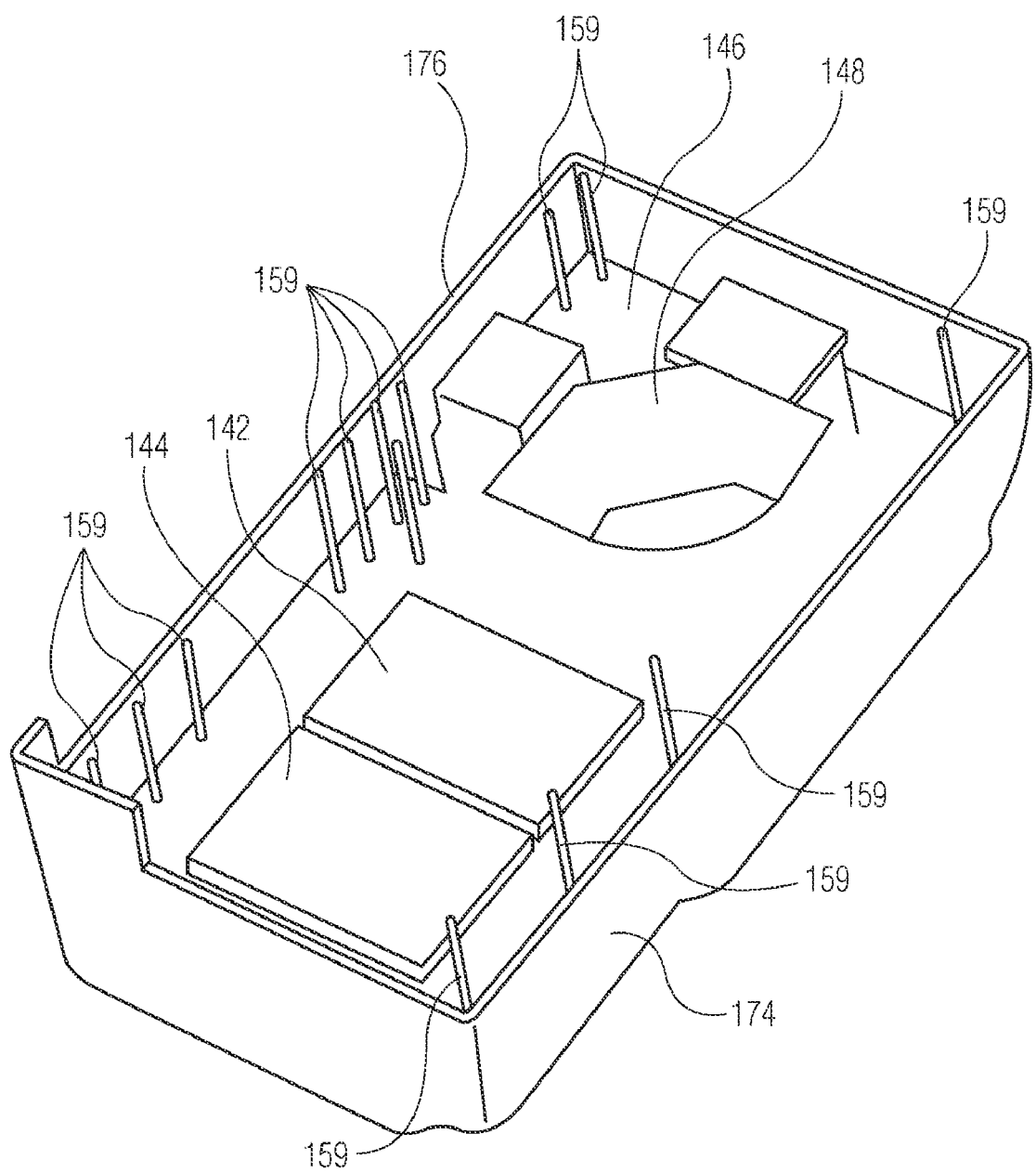
FIG. 7 is a perspective drawing of the substrate of FIG. 5 positioned in a potting shell.

FIG. 7 illustrates the substrate 140 in a potting shell 174 in which the high-voltage components will be potted in a dielectric material. The dimensions of the potting shell 174 are sufficient to accommodate placement of the substrate 140 and the high-voltage components within the shell. When placed in the potting shell 174, the signal pins 159 extend beyond the edge 176 so that when potted, the resulting high-voltage module can be electrically coupled to the remaining systems of the defibrillator 10. The potting shell 174 can be formed from material known in the art, or from materials later developed. Materials that are currently known for constructing potting shells include acrylonitrile-butadiene-styrene (ABS), nylon, polyvinyl chloride (PVC), glass filled polyester, polyphenylene oxide (PPO), polycarbonate, and various metals.

Figure 8:
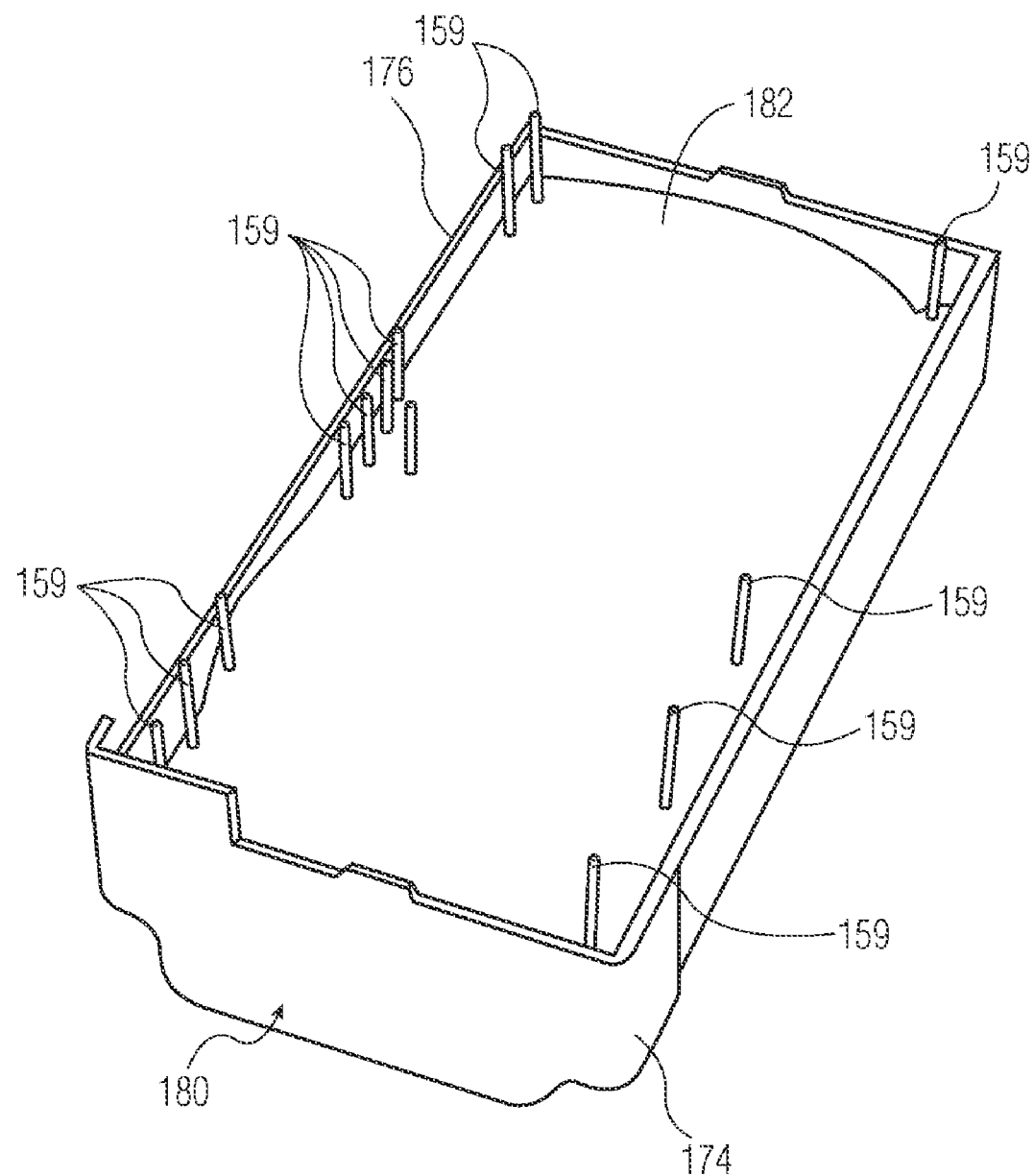
FIG. 8 is a perspective drawing of the substrate of FIG. 5 encased by the potting shell of FIG. 7 and a potting material.

FIG. 8 illustrates a high-voltage module 180 according to an embodiment of the present invention resulting from encasing the substrate 140 and the high-voltage components in a potting shell 174 and potting compound 182. As previously discussed, the signal pins 159 extend beyond the edge 176 of the potting shell 174. Additionally, the signal pins 159 extend beyond a surface of the potting compound 182 to allow the high-voltage components of the high-voltage module 180 to be electrically coupled to other systems of the defibrillator 10.

The outside dimensions of the potting shell 174 roughly define the volume of the high-voltage module 180, since the substrate 140, the high-voltage components, and the potting compound 182 are contained in the potting shell 174. As shown in FIGS. 7 and 8, the volume of the high-voltage module 180 is approximately 2.5 cubic inches. However, it will be appreciated by those ordinarily skilled in the art that the volume of a module according to an embodiment of the present invention can be different than that shown in FIGS. 7 and 8 without departing from the scope of the present invention. For example, in one embodiment of the present invention, the volume of the high-voltage module is approximately six cubic inches.

The potting compound used provides sufficient insulation for operation of the high-voltage components of the high-voltage module 180 in the defibrillator 10. Examples of potting compounds that can be used for the high-voltage module 180 include resins of epoxy, urethane, silicone, acrylic, and polyester, and thermoplastic materials as well. Materials formed from combinations of these resins can also be used. As previously discussed, some of the high-voltage components attached to the substrate 140 (FIG. 5) are packaged in device packages that are not rated for the operating conditions to which the components are subjected during normal operation of the defibrillator 10. Additionally, the high-voltage components are positioned relative to one another in closer proximity than using conventional designs for electronic circuitry operating under the typical conditions for a defibrillator. The dielectric material in which the high-voltage components and the substrate are encased provides additional resistance to voltage, temperature, and other factors to allow the high-voltage components to operate under normal operating conditions of the defibrillator 10. As a result, the high-voltage components can be attached to a smaller substrate and can be in closer proximity to each other than the high-voltage components of conventional defibrillator designs, and consequently can be assembled into a compact high-voltage module.

From the foregoing it will be appreciated that, although specific embodiments of the invention have been described herein for purposes of illustration, various modifications may be made without deviating from the spirit and scope of the invention. For example, the previous embodiment shown with respect to FIGS. 7 and 8 illustrate a high-voltage module that is potted in a potting shell 174 and potting compound 182. However, in alternative embodiments of the present invention, the substrate 140 and the high-voltage components attached to the substrate 140 are encapsulated in a dielectric material. That is, the mold used for providing shape to the dielectric material is removed after the dielectric material hardens, and does not form part of the final high-voltage module. Accordingly, the invention is not limited except as by the appended claims.

Another embodiment of the present invention is directed to a defibrillator that includes a compact high-voltage module having high-voltage electronics of the defibrillator placed in proximity to one another and encased in a dielectric material. In the following description well-known circuits have not been shown in detail in order to avoid unnecessarily obscuring the description of the various embodiments of the invention. Also not presented in any great detail are those well-known control signals and signal timing protocols associated with the internal operation of defibrillators.

Figure 9:
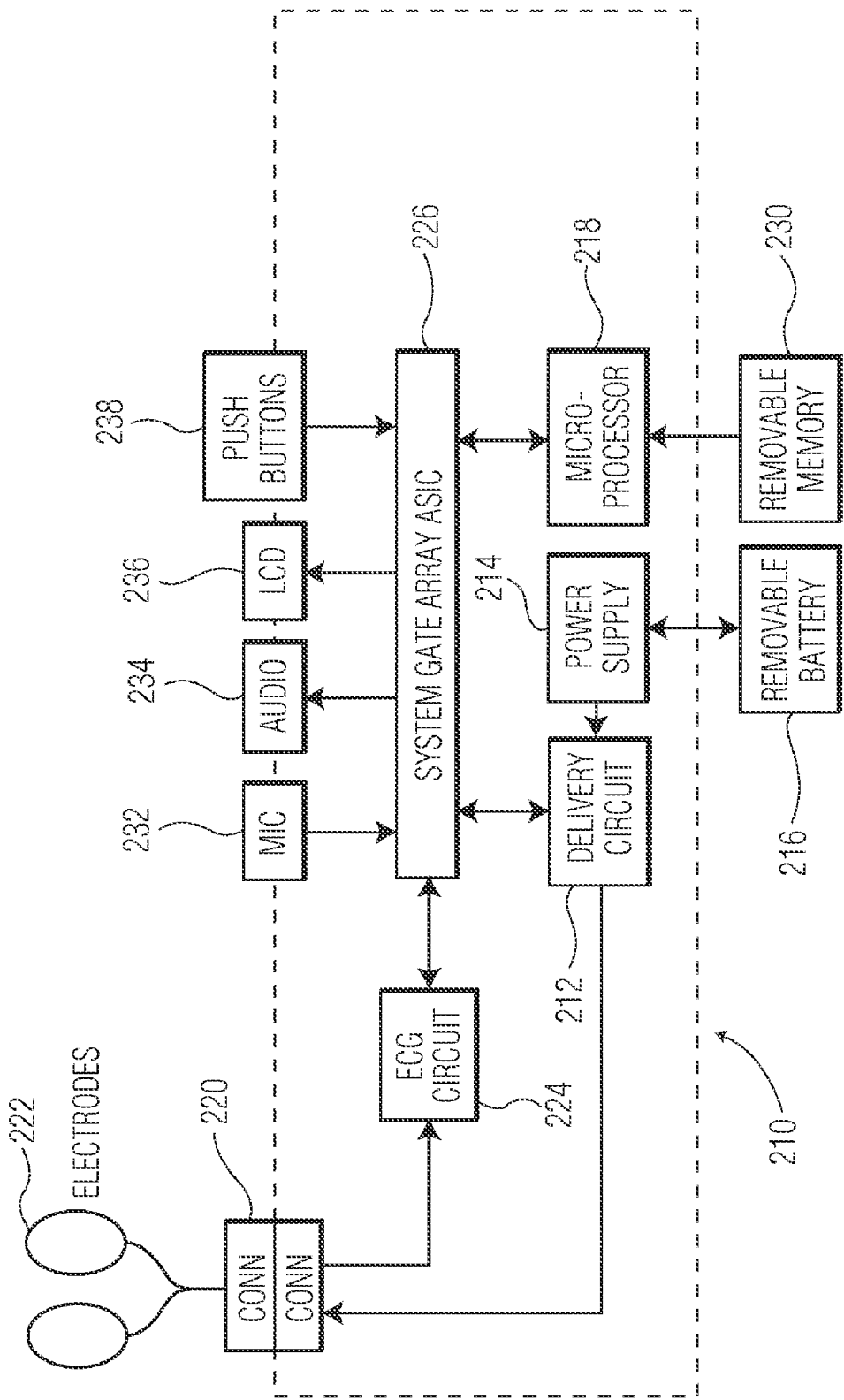
FIG. 9 is a functional block diagram of an external defibrillator according to an embodiment of the present invention.

FIG. 9 is a functional block diagram of a defibrillator or AED 210 according to an embodiment of the present invention. The AED 210 includes a delivery circuit 212 that is capable of delivering high or low voltage depending upon the application. The AED 210 further includes a power supply 214 which is powered by an energy source such as a removable battery 216 which provides power to components of the AED 210, including the high-voltage delivery circuit 212. A microcontroller or processor 218 controls the operation of the various components of the AED 210. The high-voltage delivery circuit 212 delivers a pulse of electrical energy to a patient via an electrode connector or interface 220 and patient electrodes 222.

An electrocardiogram (ECG) circuit 224 acquires and pre-conditions the patient's ECG signals acquired through the electrodes 222 and sends the signals to the processor 218 via a system gate array 226. The system gate array 226 is a custom application-specific integrated circuit (ASIC) integrating many of the defibrillator functions (including user interface control and many of the internal functions) and interfacing the processor 218 with other components of the AED 210. Providing the separate system gate array or ASIC 226 allows the processor 218 to focus on other tasks. The functionality of the ASIC 226 can be included within the operations performed by the processor 218 as well, or can be replaced by discrete logic circuit components or a separately dedicated processor.

The AED 210 also includes a memory device 230 (such as a removable Personal Computer Memory Card International Association (PCMCIA) card, Secure Digital card or flash memory), and user interface components such as a microphone 232, an audio speaker 234, an LCD display panel 236, and a set of push-button controls 238. Those skilled in the art will understand that a number of other components may be included within the AED 210 (e.g., a system monitor and associated status indicators), but are not shown in order to avoid unnecessarily obscuring the description of embodiments of the present invention.

Figure 10:
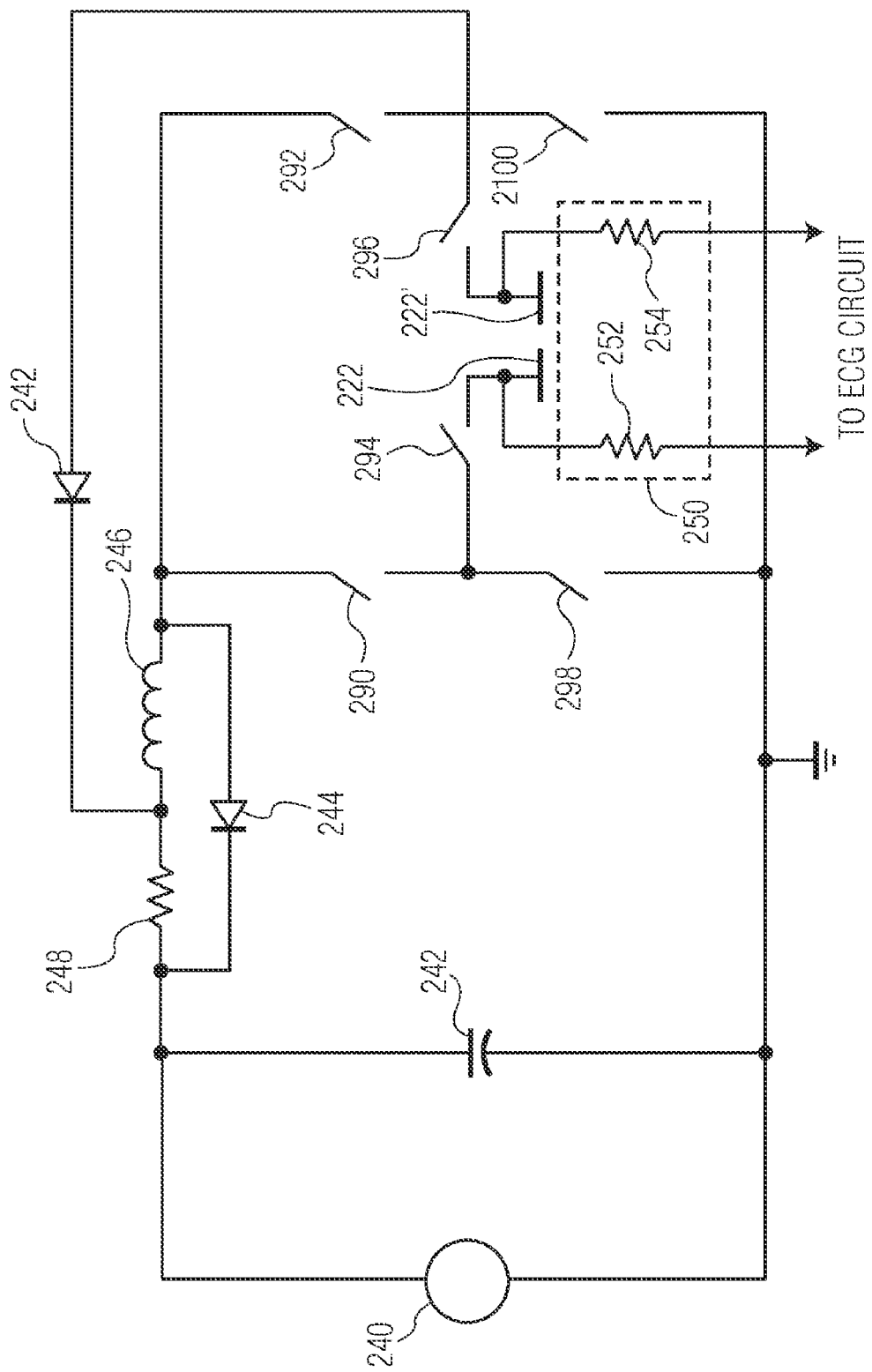
FIG. 10 is a functional block diagram of a high-voltage delivery circuit included in the defibrillator of FIG. 9.

The high voltage components of the AED of FIG. 9 are found in the power supply 214 which develops the high voltages needed for defibrillation and in the delivery circuit 212 which delivers the high voltage to the electrodes 222 and ultimately the patient. FIG. 10 is a schematic and block diagram illustration of the high voltage section of an AED constructed in accordance with the present invention. A high voltage power supply or charger 240 operates to charge the energy storage capacitor 242 for delivery of a defibrillating pulse. The high energy pulse is applied by way of a resistor 248 which serves to limit the current on discharge of the capacitor. During normal pulse delivery switches 294 and 296 are closed to connect the energy delivery circuit 212 to the electrodes 222 which are applied to the patient. Switches 294 and 296 are safety switches which are opened when the capacitor 242 is charged while the patient's ECG waveform is being monitored to prevent accidental discharge of high voltage to the patient and ECG circuits during charging. Four switches 290, 292, 298 and 200 are used in conjunction with switches 294 and 296 in an "H-bridge" configuration. When a biphasic pulse is to be delivered to the patient, switches 290 and 2100 are closed and switches 292 and 298 are left opened. The high voltage energy will then flow through the closed switches and from the left electrode 222 and through the patient to the right electrode 222'. After the first phase of the biphasic pulse has been delivered the second phase of the pulse is delivered by opening switches 290 and 2100 and closing switches 292 and 298. The high voltage current will then flow through the patient in the opposite direction, from electrode 222', through the patient, and through electrode 222. Thus, the H-bridge delivery circuit is a means by which a biphasic pulse can be delivered to the patient.

Also connected to the electrodes 222 is an ECG front end circuit 250 by which the electrodes 222 are used to detect the patient's ECG waveform when defibrillating pulses are not being delivered. When the patient's ECG waveform is being detected and analyzed the safety switches 294 and 296 are opened and the patient's ECG signal is applied to the input of one or more ECG input amplifiers across the impedances 252 and 254.

The delivery circuit 212 in the illustrated embodiment also includes a series inductor 246 which, together with the resistor 248, serves to limit the rate of current rise of an applied high voltage pulse. A diode 244 clamps the inductance of the inductor 246 any time that current in the delivery circuit is turned off, such as at the end of the first phase of the pulse. A diode 242 clamps the inductance of the electrode wires to the patient at the end of the first phase of the pulse.

In one embodiment the switches 290, 292, 298 and 2100 are not mechanical switches but are solid-state switching devices. In this embodiment switches 290, 292, and 298 are SCRs (silicon-controlled rectifiers) and switch 2100 is an IGBT (insulated gate bipolar transistor). With safety switches 294 and 296 closed, a biphasic pulse is delivered to the patient by first switching SCR 290 and IGBT 2100 to the conductive state. There is an initial rise in current after which the positive pulse undergoes a controlled decay. After a predetermined time for the positive pulse the IGBT 2100 is opened and the voltage and current of the positive pulse drop to zero. SCR 290 then returns to a blocking state. Shortly thereafter SCRs 292 and 298 are switched to the conductive state and there is a rapid rise of the negative pulse, followed by a controlled decay of the pulse. After a predetermined period for the negative pulse SCR 290 is made conductive, bringing the current and voltage applied to the patient to zero again. When the flow of current stops the SCRs turn off and return to the blocking state. The H-bridge is then in its initial state and ready for the next pulse sequence.

In accordance with the principles of the present invention high voltage components of the high voltage capacitor charging circuit, the high voltage delivery circuit and the H-bridge circuit are assembled in a high voltage module. In a constructed embodiment the module includes a multi-layer circuit board on which the H-bridge semiconductor switches and diodes, isolation transformers and control circuits for the semiconductor switches, and the transformer and diodes of the high voltage capacitor charging circuit are mounted. The constructed embodiment utilizes standard discrete surface mount semiconductor packages, control circuits and isolation transformers. The constructed module also integrates a planar transformer for the capacitor charger which utilizes etched conductors on the circuit board for the transformer windings. By encapsulating the module in a dielectric such as an epoxy, urethane, silicone, acrylic, or polyester resin, the creepage and clearance distances needed to prevent arcing can be reduced, enabling a more compact package. By combining a plurality of high voltage components into a single module only one potting cup and encapsulation process is required, which reduces the cost of system manufacture.

Figure 11:
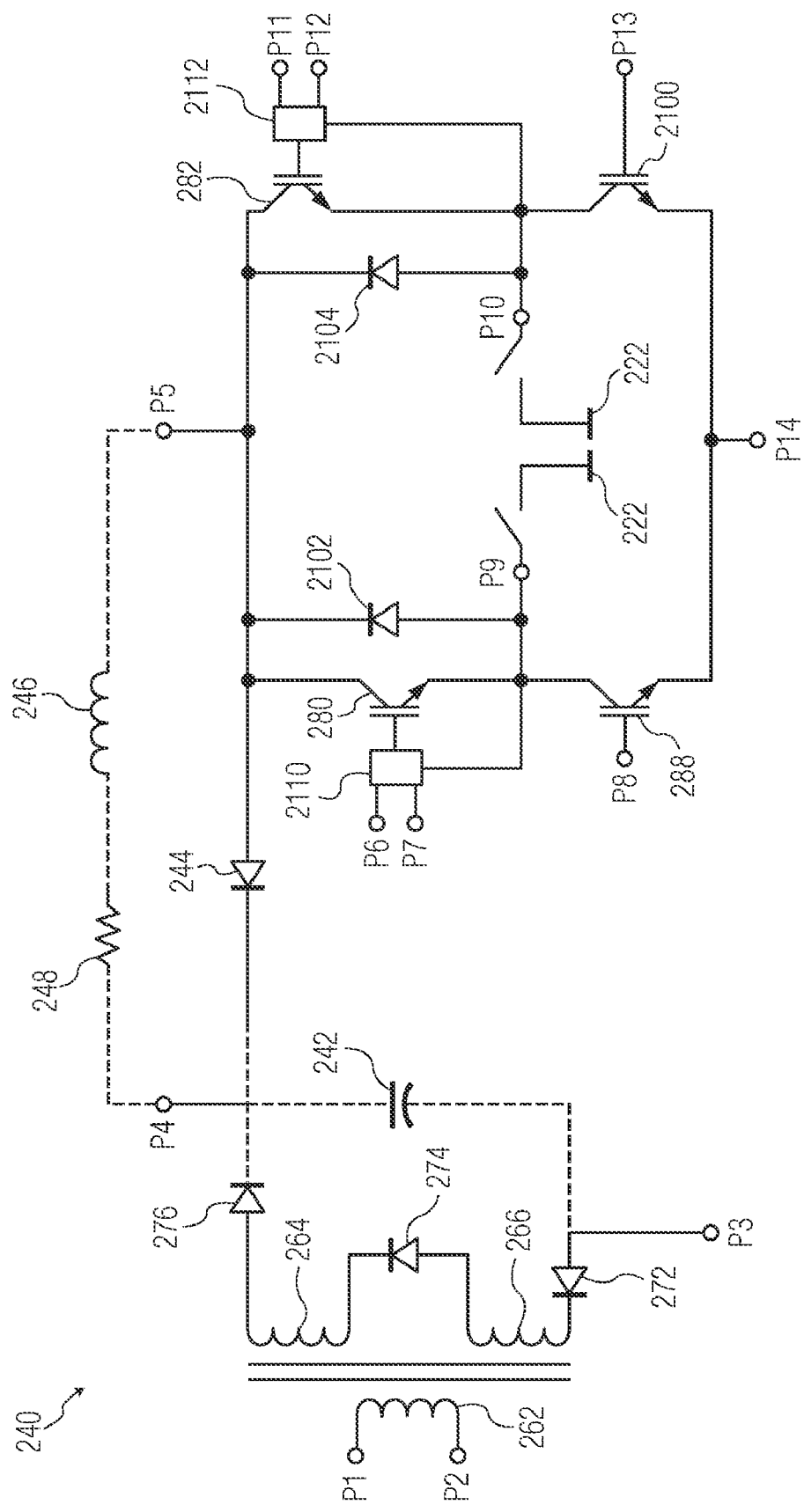
FIG. 11 is a schematic diagram showing high voltage components which are modularly packaged in accordance with the principles of the present invention.

Referring to FIG. 11 the components of a high voltage module constructed in accordance with the principles of the present invention are shown in solid lines. The module is mounted on the AED system circuit board (not shown), where connections are made to other components shown in dashed lines. Fourteen pins, labeled P1 through P14, are used to connect the circuitry of the high voltage module to other conductors and components of the AED. At the left side of the drawing is the charger circuit 240, including a transformer having a primary coil 262 and secondary coils 264 and 266. The secondary windings are separated by diodes 272, 274, and 276 which provides symmetrical design in which stray capacitances are balanced. In a constructed embodiment the charger transformer is formed as a planar transformer in which the coils 262, 264, and 266 are formed by opposing areas of etched copper of the module printed circuit board around which ferrite core halves forming the transformer core are clamped. The high voltage capacitor 242 is connected to pins P3 and P4 of the module. Pins P4 and P5 are connected to the external current limiting resistor 248 and inductor 246. The clamping diode 244 is located on the module and connected between pins P4 and P5.

In accordance with a further aspect of the present invention, in this embodiment the switching devices 290, 292, 298 and 2100 are provided by four semiconductor IGBT devices 280, 282, 288, and 2100. High voltage IGBT devices are used, preferably with a voltage rating in excess of 2000 volts. The use of IGBTs for all of the switching devices provides better control of energy delivery over a full range of 2-200 Joules. The IGBTs will remain conductive at very low current levels and can be controllably turned off, as opposed to SCRs which remain conductive so long as a sufficient supply of current is available. Once turned on, SCRs will remain conductive as long as at least the minimum hold current is maintained. The SCRs will not turn off until the current supply is reduced below the minimum hold current for the devices. The use of IGBTs for the switching devices of the H-bridge enables an embodiment of the present invention to be used for lower voltage applications such as pacing in addition to defibrillation. The IGBTs are also not as sensitive to rapid current and voltage rises as are SCRs. The collectors of the upper pair of IGBTs 280 and 282 are coupled to the pin P5 to receive the high voltage and current from the high voltage capacitor 242. The emitters of the IGBTs 280 and 282 are coupled to pins P9 and P10 which connect to the electrodes 222. Shunt diodes 2102 and 2104 are coupled across the collector-emitter paths of the IGBTs 280 and 282. The IGBTs are controlled by driver circuits including gate drive transformers coupled to the gates of the IGBTs 280 and 282. The two lower IGBTs 288 and 2100 of the H-bridge circuit are coupled between the upper IGBTs and pin P14, which is coupled to reference potential.

Figure 12:
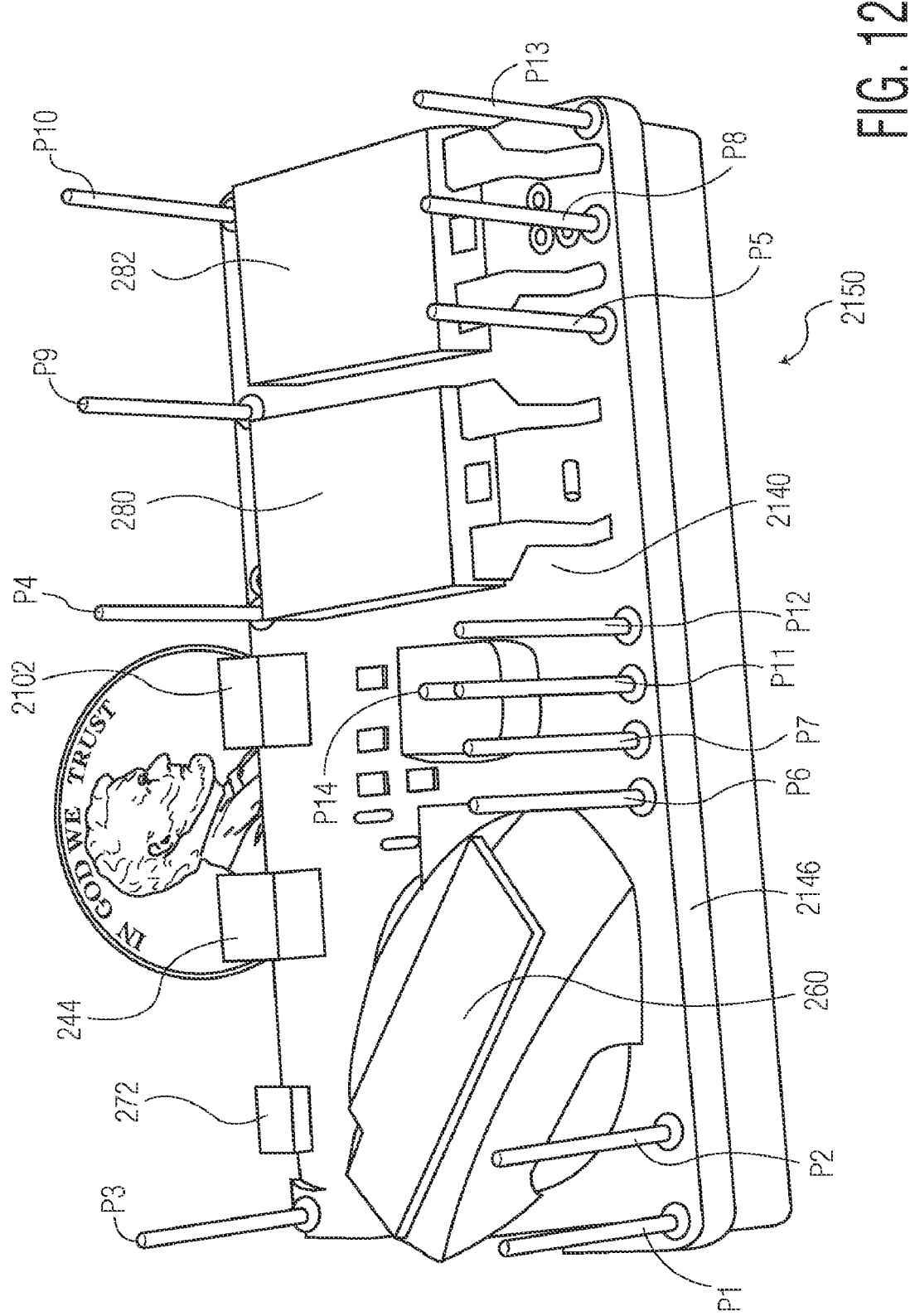
FIG. 12 is a perspective view of one side of a high-voltage module according to an embodiment of the present invention.

FIG. 12 illustrates the high voltage circuit elements of FIG. 11 assembled in a unitary high voltage module 2150. (A US one cent piece is shown behind the module to enable the viewer to gauge the size of the module.) The components are mounted on a substrate which in this embodiment is a multi-layer printed circuit board 2140. The connecting pins P1-P14 are seen to extend upward from the board 2140 in this picture. In this embodiment the components are mounted on both sides of the printed circuit board in a symmetrical arrangement. The planar transformer 260 is located on the left side of the board 2140. A thin disk of white plastic is partially visible which is an insulator for the transformer coil etched on this side of the printed circuit board. The white plastic disk is mostly obscured in this view by the ferrite core half clamped over the disk which forms a portion of the core of the planar transformer. Behind pins P6, P7, P11, P12, P14 is one of the isolation transformers of an IGBT trigger circuit 2112 together with surface mounted components of the trigger circuit. At the rear of the board are three of the diodes 272, 244 and 2102. On the right side of the board are two of the IGBT devices 280 and 282. In the FIG. 12 embodiment, the dimensions of the substrate to which the components are mounted are approximately 1.25 inches by 2.25 inches. In alternative embodiments, the substrate to which the high-voltage components are attached can have different dimensions than shown in FIG. 12. In one embodiment of the present invention, the substrate has dimensions such that one side of the substrate has a surface area of less than five square inches.

Figure 13:
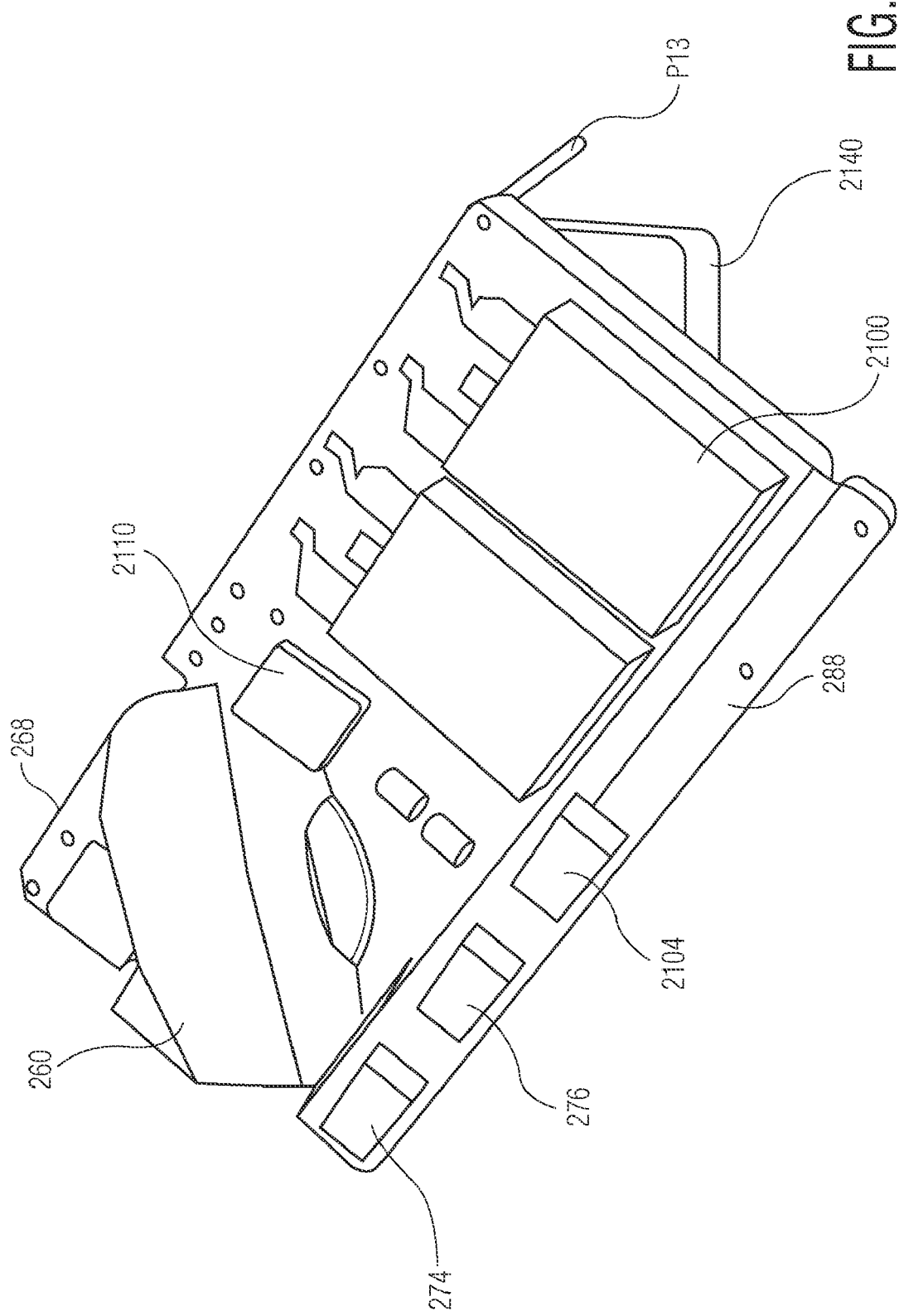
FIG. 13 is a perspective view of the second side of the high-voltage module of FIG. 12.

FIG. 13 shows the reverse side of the printed circuit board 2140. The other half of the planar transformer 260 is seen at the top of the illustration, including the other portion of the ferrite core 268. The other three diodes of the module, 274, 276, 2104 are mounted opposite the first three diodes on the other side of the board. The isolation transformer of trigger circuit 2110 is seen in the center of the board, opposite the isolation transformer on the other side of the board. IGBT devices 288 and 2100 are mounted opposite the IGBT devices on the other side of the board.

Figure 14:
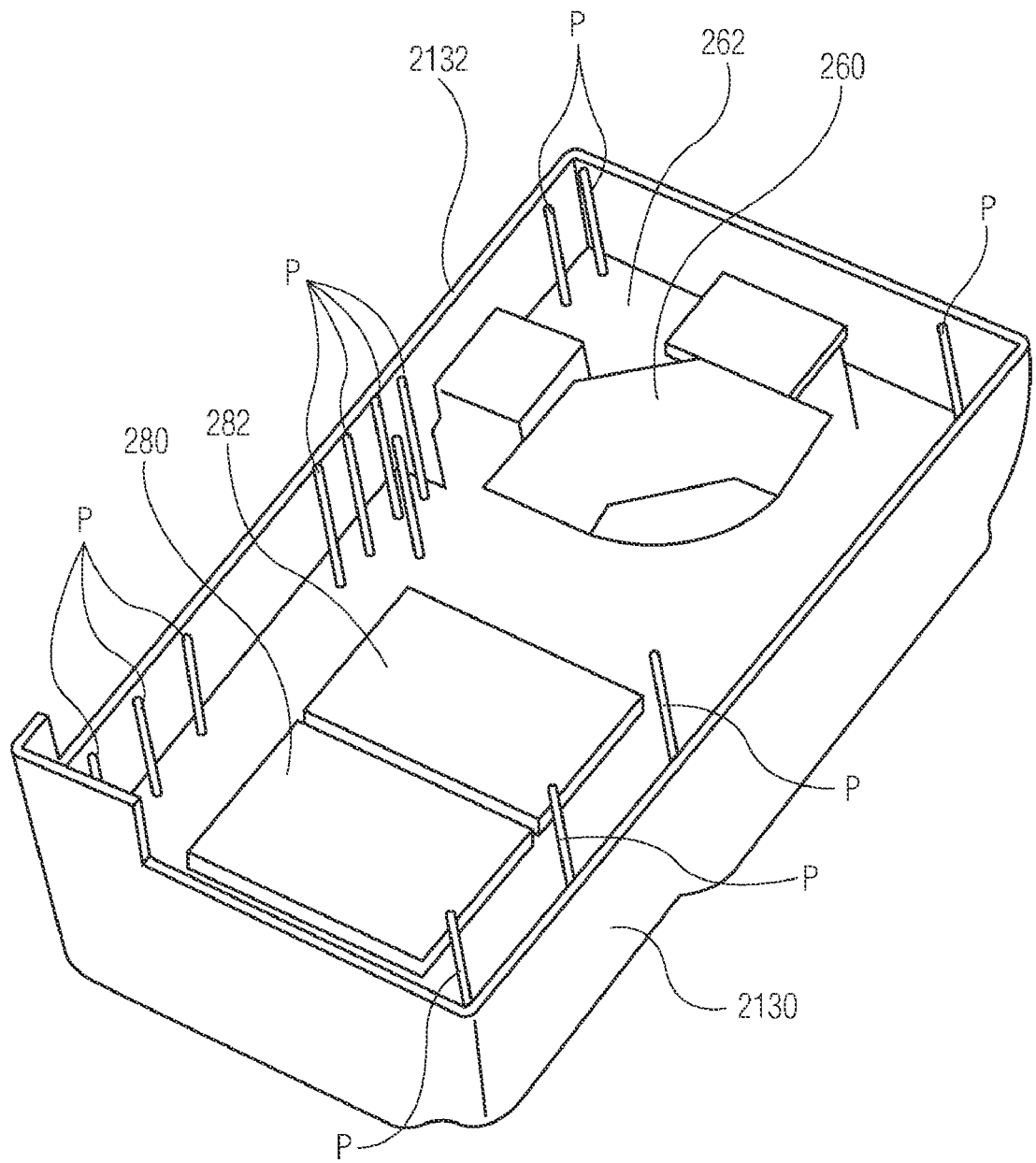
FIG. 14 is a perspective view of the high-voltage module of FIG. 13 positioned in a potting cup.
Figure 15:
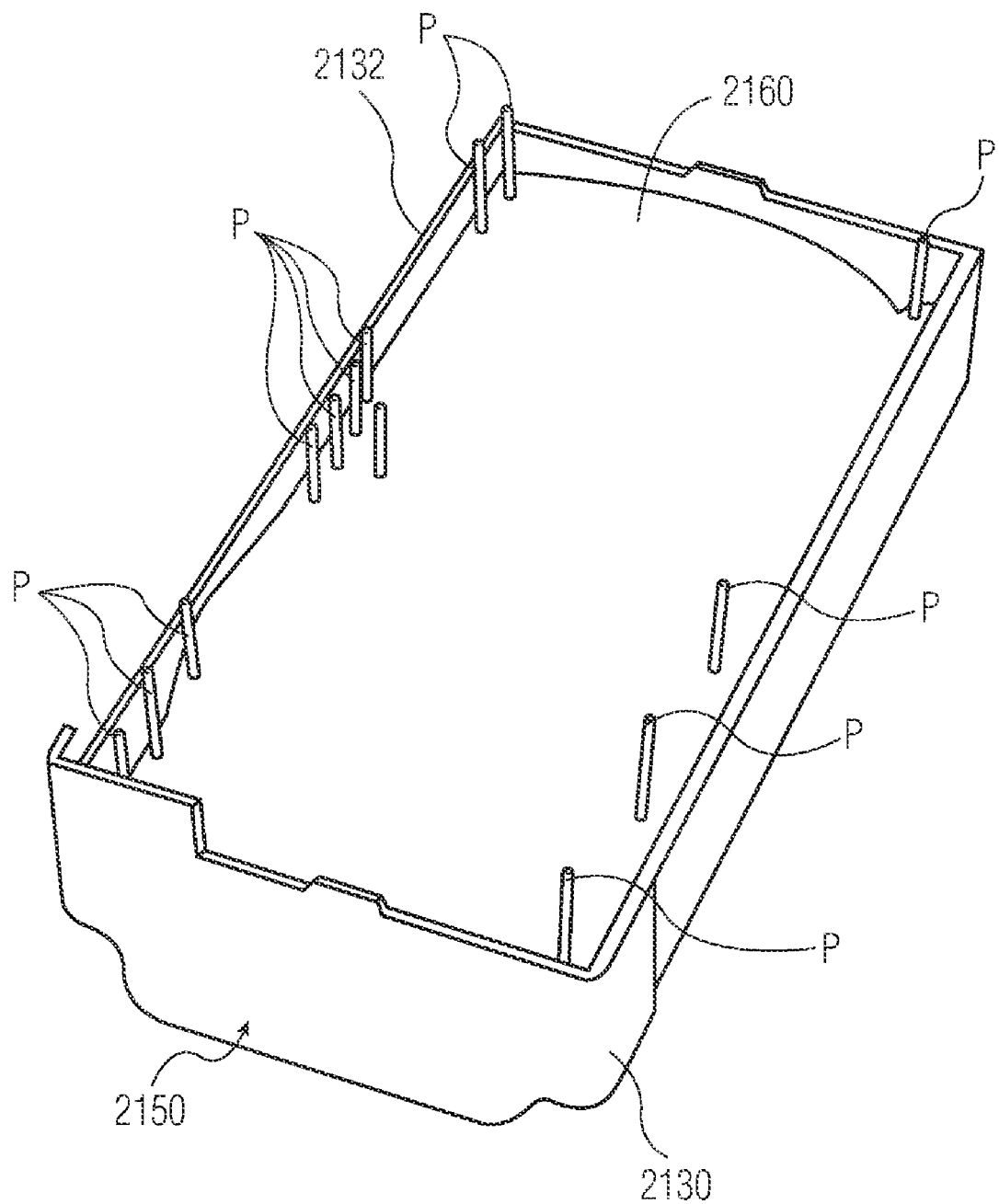
FIG. 15 is a perspective view of the high-voltage module of FIG. 13 encased by a potting material.

In FIG. 14 the printed circuit board 2140 with its mounted components is shown in a plastic potting cup 2130. The fourteen pins, all labeled P in this illustration, extend upward in this view above the edge 2132 of the potting cup. The potting cup 2130 is then filled with a potting compound 2160 which completely encapsulates the board and high voltage components as shown in FIG. 15. The potting compound thereby provides an insulating dielectric around and between all of the high voltage components. The potted board and components can be removed from the potting cup and used in that configuration. In the constructed embodiment the potted board and components is left in the potting cup and the entire high voltage module 2150 including the potting cup 2130 is mounted on the AED system printed circuit board. The module is compact and takes up less space on the system printed circuit board than would the individually mounted components, and the potting cup and dielectric potting compound provide an insulation layer which prevents arcing between the high voltage components and nearby low voltage nodes, conductors, and components. As shown in FIGS. 14 and 15, the volume of the high-voltage module 2150 is approximately 2.5 cubic inches. However, it will be appreciated by those ordinarily skilled in the art that the volume of a module according to an embodiment of the present invention can be different than that shown in FIGS. 14 and 15 without departing from the scope of the present invention. For example, in one embodiment of the present invention, the volume of the high-voltage module 2150 is approximately six cubic inches.

Other embodiments will readily occur to those skilled in the art. For example, instead of arranging the switching devices in a full H-bridge circuit, only a half-bridge circuit consisting of two switching devices on one side of the bridge and two capacitors on the other side of the bridge may be used.

What is claimed is:

1. An external defibrillator for delivering an electrical pulse at a high voltage suitable for defibrillation comprising:
   a pair of patient electrodes for delivering energy to a patient;
   an energy storage device for storing high voltage electrical energy; and
   a modularly packaged high voltage circuit coupled between the energy storage device and the patient electrodes, the high voltage circuit including a circuit board and a plurality of high voltage components which are mounted on the circuit board, and wherein the high voltage circuit is encased in a non-air dielectric material.

2. The external defibrillator of claim 1 wherein dielectric material comprises means for preventing arcing between the modularly packaged high voltage circuit and a nearby low voltage conductor or component.

3. The external defibrillator of claim 1 wherein the high voltage circuit includes a high voltage energy delivery circuit.

4. The external defibrillator of claim 3 wherein the high voltage energy delivery circuit includes an H-bridge circuit.

5. The external defibrillator of claim 4 wherein the H-bridge circuit includes a plurality of switches which are modularly packaged.

6. The external defibrillator of claim 5 wherein the switches comprise semiconductor devices.

7. The external defibrillator of claim 6 wherein the semiconductor devices are chosen from types of SCRs and IGBTs.

8. The external defibrillator of claim 1 wherein the high voltage components are symmetrically mounted on opposite sides of a the circuit board.

9. The external defibrillator of claim 1 wherein the high voltage components include a planar transformer.

10. The external defibrillator of claim 9 wherein at least one of the windings of the planar transformer is etched on the circuit board.

11. The external defibrillator of claim 1 wherein the modularly packaged high voltage components and circuit board further includes a plurality of pins by which the modularly packaged high voltage components and circuit board are electrically connected to an AED circuit.

12. The external defibrillator of claim 11 wherein the modularly packaged high voltage components and circuit board are encased in a dielectric material, wherein the pins extend from the dielectric material.

13. The external defibrillator of claim 11 wherein the modularly packaged high voltage components and circuit board are located in a potting cup and encased in a dielectric material inside the potting cup.

14. An external defibrillator, comprising:
   a pair of electrodes for delivering defibrillating energy to a patient;
   a capacitor for storing electrical energy;
   a circuit board having a processor which processes an ECG waveform; and
   a high voltage module including a plurality of high voltage components for at least one of charging the capacitor and delivering high voltage energy suitable for defibrillation to the electrodes, the high voltage components being potted in a non-air dielectric material,
   wherein the high voltage module is mounted on the circuit board.

15. The external defibrillator of claim 14 wherein the high voltage module includes a high voltage component for charging the capacitor and an H-bridge circuit for delivering capacitor energy to the electrodes.

16. The external defibrillator of claim 14 wherein the high voltage module includes
   a printed circuit board on which the high voltage component are mounted;
   a potting cup in which the circuit board is located;
   a dielectric material encasing the printed circuit board and high voltage components; and
   a plurality of pins extending from the dielectric material for electrically connecting the module to the circuit board.

17. The external defibrillator of claim 16 wherein the dielectric material encasing the printed circuit board and high voltage components comprises a resin formed from at least one, including a combination, of epoxy, urethane, silicone, acrylic, and polyester resins.

18. A modularly packaged high voltage module for delivering high voltage external defibrillation pulses comprising:
   a circuit board;
   a plurality of high voltage components mounted on the circuit board; and
   a non-air dielectric material encasing the circuit board and the plurality of high voltage components, wherein the volume of the high voltage module is between 2½ cubic inches and 6 cubic inches.

19. A modularly packaged high voltage module for delivering high voltage external defibrillation pulses comprising:
   a circuit board;
   a plurality of high voltage components mounted on the circuit board; and
   a non-air dielectric material encasing the circuit board and the plurality of high voltage components,
   wherein the surface area of one side of the circuit board is less than 5 square inches.

* * * * *